(12) United States Patent
Laghi

(10) Patent No.: US 6,797,009 B1
(45) Date of Patent: Sep. 28, 2004

(54) PROSTHETIC FOOT WITH HEEL OF ELASTICITY

(76) Inventor: Aldo A. Laghi, 14410 Eagle Point Dr., Clearwater, FL (US) 33762

(*) Notice: Subject to any disclaimer, the term of this patent is extended or adjusted under 35 U.S.C. 154(b) by 0 days.

(21) Appl. No.: 10/064,845

(22) Filed: Aug. 22, 2002

(51) Int. Cl.⁷ .................................................. A61F 2/66
(52) U.S. Cl. ....................................................... 623/53
(58) Field of Search ..................................... 623/47–56

(56) References Cited

U.S. PATENT DOCUMENTS

| | | | | |
|---|---|---|---|---|
| 5,116,383 A | * | 5/1992 | Shorter et al. ................ | 623/49 |
| 5,258,039 A | * | 11/1993 | Goh et al. .................... | 623/55 |
| 5,314,499 A | * | 5/1994 | Collier, Jr. ................... | 623/47 |
| 5,571,210 A | * | 11/1996 | Lindh .......................... | 623/38 |
| 5,653,767 A | * | 8/1997 | Allen et al. .................. | 623/52 |
| 5,695,527 A | * | 12/1997 | Allen ........................... | 623/55 |
| 5,800,570 A | * | 9/1998 | Collier ......................... | 623/55 |
| 5,944,760 A | * | 8/1999 | Christensen ................ | 623/55 |
| 6,007,582 A | * | 12/1999 | May ............................. | 623/55 |
| 6,514,293 B1 | * | 2/2003 | Jang et al. .................... | 623/55 |
| 6,602,295 B1 | * | 8/2003 | Doddroe et al. .............. | 623/55 |
| 2002/0013628 A1 | * | 1/2002 | Harris .......................... | 623/55 |
| 2002/0087216 A1 | * | 7/2002 | Atkinson et al. ............. | 623/38 |
| 2003/0009238 A1 | * | 1/2003 | Whayne ....................... | 623/32 |
| 2003/0045944 A1 | * | 3/2003 | Mosler et al. ................ | 623/52 |

* cited by examiner

*Primary Examiner*—Alvin Stewart
(74) *Attorney, Agent, or Firm*—Ronald E. Smith; Smith & Hopen, P.A.

(57) ABSTRACT

A dynamic prosthetic foot has a heel of elasticity made of a lateral heel and a medial heel that are formed separately from one another. A lateral ankle diverges upwardly from a sole along a transverse parting line and includes a horizontal and a vertical part that collectively form a lateral ankle part. The horizontal part is supported by a return bend formed in the lateral heel. The medial heel includes a return bend formed integrally with the sole but includes no medial ankle upper part. Each of the two heel parts independently absorbs impacts generated during ambulation and therefore provides differentiated heel elasticity. The lateral heel transfers loads to the medial heel because the lateral ankle upper part is supported by the lateral heel and the return bend that forms the medial heel is unsupported.

16 Claims, 4 Drawing Sheets

PROSTHETIC FOOT WITH HEEL OF ELASTICITY

BACKGROUND OF THE INVENTION

1. Field of the Invention

This invention relates, generally to the art of prosthetics. More particularly, it relates to improvements in prosthetic feet.

2. Description of the Prior Art

During normal ambulation, the first part of a foot to contact the ground is the trailing end of the heel. This initial contact between heel and ground is known as the "heel strike." The trailing end of the heel is soft and thus cushions the heel strike to at least some extent. The hard bottom of the heel is the next part of the foot to strike the ground; its hardness allows it to support the entire weight of the body. The foot continues to rotate in the well-known way until the toes "push off" at the end of a step.

Early prosthetic feet are quite rigid and provide little or no cushion to the impact on the ground at the moment of "heel strike" and little or no elastic response at "push off." The shock of impact is thus transmitted directly to the skeletal structure of the user, and the lack of elastic response forces an unnatural gait.

Perhaps the earliest prosthetic foot that provides an elastic response at heel strike and push off is disclosed in U.S. Pat. No. 4,547,913 to Phillips, assigned to Flex Foot, Inc. Multiple versions of that device have been developed. The original version is formed of a carbon fiber-epoxy matrix consisting of a one-piece combination pylon upper and a one-piece sole. Mechanical fasteners interconnect the upper and the sole. In a second embodiment, the pylon is a round hollow tube and is connected by mechanical fasteners to a rectangular-shaped upper. A third version is like the first except that a standard Sach® foot adapter is employed to connect a standard prosthetic pylon. A fourth version is like the third but has a slightly different geometry. In a fifth version, an elastomeric glue connects the upper and the sole. In additional embodiments, leaf springs or hydraulic cylinders are incorporated into the prosthetic foot.

Although the developments in the art since the mid 1980s have significantly advanced the technology of prosthetic feet, the known prosthetic feet still provide little or no heel elasticity in a direction parallel to the ground. Instead, they provide elastic response in a vertical plane. Thus, although the impact at heel strike is reduced vis a vis the pre-1980's prosthetic feet, the reduced impact is transmitted vertically to the skeletal structure of the user, and the elastic response in a vertical plane causes a four to six millimeter bounce at heel strike. This vertical response causes an unnatural walk because a healthy human heel is soft at the trailing end where heel strike occurs and is hard on the bottom so that it can support the entire weight of the body. Thus, the normal gait of a human includes a rolling motion as the tailing end of the heel strikes the ground; there is no vertical motion causing the heel to bounce upon ground impact.

Accordingly, there is a need for a prosthetic foot that provides substantial heel elasticity in a direction parallel to the ground.

A healthy human foot rolls on the lateral part of the foot during ambulation. The medial part of the foot provides a cushion and the force required at push off. Thus, there is a smooth transition from heel strike to push off, with no vertical dynamic response of the type that could cause the foot to bounce. Prosthetic feet of the type heretofore known, however, do not provide a smooth transition from heel strike to push off. This lack of a smooth transition produces what is known in the industry as a "flat spot." The presence of a flat spot between heel strike and push off produces an unnatural gait.

More particularly, the dynamic response is primarily vertical at the heel and the toe of a prosthetic foot. There is little or no component of the dynamic response in a horizontal plane as present in a healthy natural foot. The absence of dynamic response in a horizontal plane results in a step like motion going from an elastic vertical motion at heel strike to little or no support at mid-stance (the flat spot), and then again to an elastic vertical motion at push off.

There is a need, therefore, for a prosthetic foot having a dynamic response in a horizontal plane during heel strike, that provides a smooth transition between heel strike and push off to eliminate the flat spot, and that provides a dynamic response in a horizontal plane during push off.

The human foot provides a more rigid support laterally than medially. This design is advantageous because when an instability occurs, the weight of the person shifts from the rigid outer or lateral edge of the foot to the less rigid inner or medial edge. In this way, the prosthetic foot takes advantage of the presence of the natural foot, i.e., the lateral-to-medial motion experienced at the moment of an instability shifts additional support duties to the natural foot. One major drawback of the heretofore known prosthetic feet is the fact that such feet provide an exactly vertical response during ambulation with no component toward the medial section of the foot. Thus, if an instability in one foot urges the person to fall away from the natural foot, there is no shift of weight toward the medial part of the prosthetic foot as would occur in a natural foot, and the likelihood of a fall is substantially increased.

A prosthetic foot is therefore needed that has differentiated medial and lateral stiffness so that it can respond to instabilities in much the same way as a natural foot.

However, in view of the prior art considered as a whole at the time the present invention was made, it was not obvious to those of ordinary skill in the pertinent art how the identified needs could be fulfilled.

SUMMARY OF THE INVENTION

The long-standing but heretofore unfulfilled need for an improved dynamic prosthetic foot is now met by a new, useful, and nonobvious dynamic prosthetic foot having a split upper ankle and a heel with differentiated elasticity. The novel prosthetic foot includes a sole, a lateral heel, and a medial heel. A lateral ankle part separates from said sole along a transverse parting line and includes a gradual upward bend, a horizontal part, and a vertically extending part. The vertically extending part providing a lateral pylon support. A lateral pylon connector is secured to the lateral pylon support on a trailing side thereof. The transverse parting line is approximately halfway between a leading end of the sole and a trailing end of the medial heel.

The lateral heel has a leading part that underlies and supports the horizontal part of the ankle part and a return bend is formed in a trailing end of the lateral heel. The return bend has a radius of curvature and terminates in a free leading end that is angled slightly upwardly relative to a horizontal plane so that a convexity near the free end is adapted to be in abutting engagement with a support surface during ambulation.

A medial heel extension is formed integrally with the sole and separates from the lateral ankle part along the transverse parting line. The medial heel extension includes a medial heel formed integrally with the medial heel extension and is adapted to abut the support surface during ambulation. The medial heel has a return bend formed therein, a horizontal part, and a vertically extending part formed integrally with the horizontal part. The vertically extending part of the medial heel provides a medial pylon support. A medial pylon connector is secured to the medial pylon support on a trailing side thereof. The medial heel has a trailing end that trails the trailing end of the lateral heel.

The lateral heel and the medial heel provide differentiated elastic responses to impact forces created by ambulation.

The horizontal part of the lateral ankle part and the horizontal part of the medial heel are co-planar with one another.

A concavity is formed about mid-length of the sole to perform the function of an arch of a natural foot. A convexity is formed about mid-way between the concavity and a toe end of the prosthetic foot. The convexity performs the function of a ball of a natural foot.

In a second embodiment, the lateral and medial pylon supports and pylon connectors are supplanted by elongate lateral and medial pylons that are about twenty inches (20") in length. A prosthetist cuts the pylons as needed when fitting the novel foot to a prosthetic socket.

The elongate lateral and medial pylons are laminated at respective uppermost ends thereof to a prosthetic socket or are connected at respective uppermost ends thereof to a connector member that is laminated to the prosthetic socket.

Alternatively, the lateral and medial pylons are connected at respective uppermost ends thereof to a pyramid-receiving connector that engages a pyramid that depends from the prosthetic socket.

An important object of this invention is to provide a prosthetic foot having heel elasticity in a direction parallel to the ground.

Another important object is to provide a prosthetic foot having a smooth transition from heel strike to push off.

Yet another object is to provide a prosthetic foot having differentiated medial and lateral stiffness so that an instability tends to shift weight from the lateral edge of the prosthetic foot to the medial edge thereof, just as in a natural foot.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
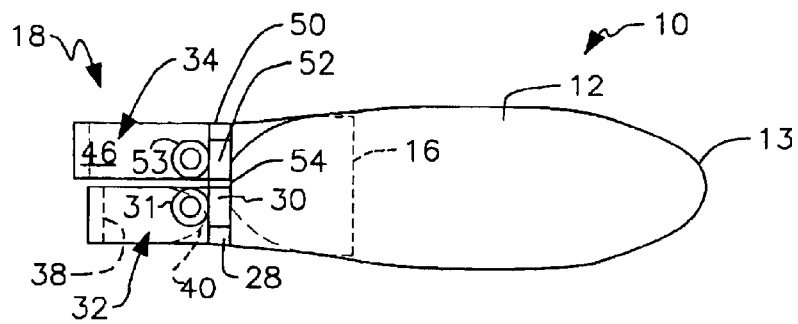
FIG. 1 is a top plan view of a prosthetic foot with a heel of elasticity.
Figure 2:
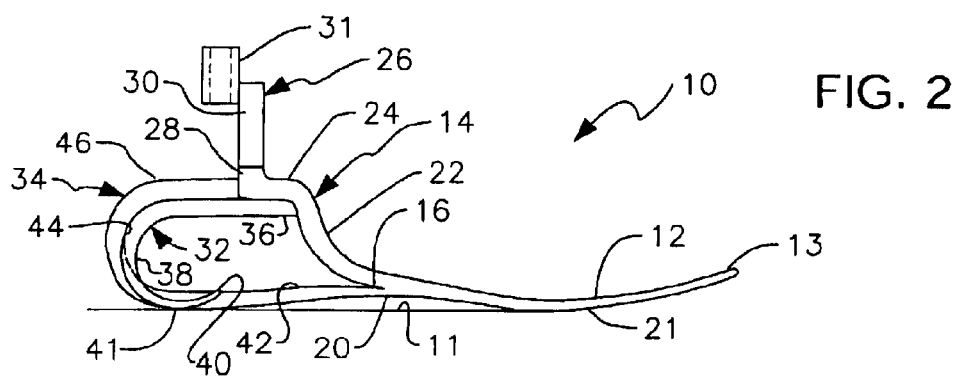
FIG. 2 is a side elevational view thereof.
Figure 3:
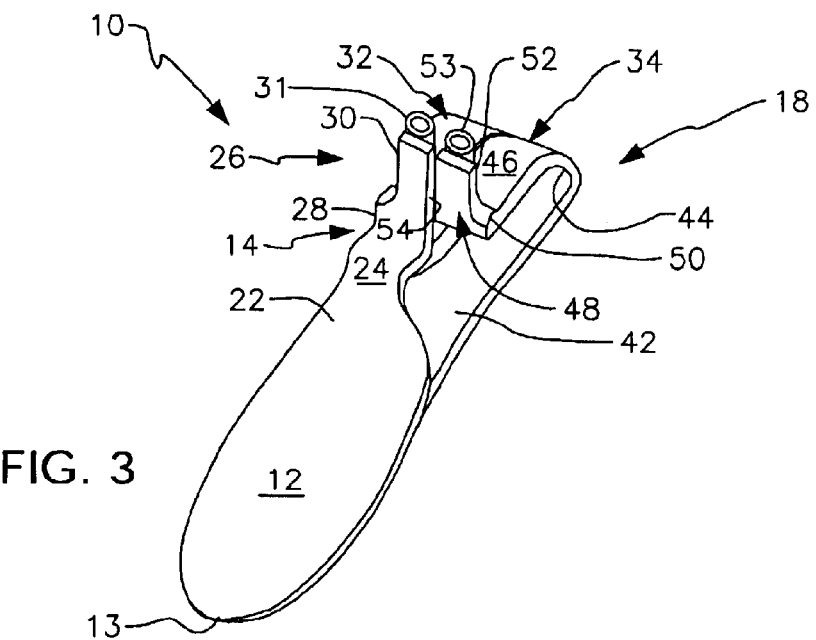
FIG. 3 is a perspective view thereof.

Referring to FIGS. 1–3, it will there be seen that the reference numeral 10 denotes an illustrative embodiment of the novel dynamic prosthetic foot with differentiated heel elasticity.

Prosthetic foot 10 includes a sole 12, a lateral ankle part 14 that separates from sole 12 at transverse parting line 16, and a heel 18 that is divided into a lateral heel 32 and a medial heel 34. Transverse parting line 16 is about mid-length of foot 10, being a little closer to the heel end thereof than the toe end.

Concavity 20 formed about mid-length of sole 12 performs a function corresponding to the function performed by the arch of a natural foot. Convexity 21 is formed about mid-way between said concavity 20 and toe end 13 of foot 10 and performs a function corresponding to the ball of a natural foot.

As best understood in connection with FIG. 3, ankle part 14 is formed on the lateral side only of prosthetic foot 10, there being no corresponding medial ankle part as best understood in connection with FIG. 3.

As best understood in connection with FIGS. 2 and 3, ankle part 14 includes a first upwardly-turned (with respect to sole 12) gradual bend 22, horizontal part 24, and lateral vertically extending part 26. As best understood in connection with FIG. 3, lateral vertically extending part 26 includes a lower part 28 having a breadth equal to that of horizontal part 24 and an upper part 30 of reduced breadth.

Upper part 30 provides a lateral pylon support. A lateral pylon, not shown, is secured by lateral pylon connector 31 to a trailing (heel) side of pylon support 30.

Lateral heel 32 has a horizontally disposed leading part 36 (FIG. 2) that underlies and supports horizontal part 24 of lateral ankle part 14. A downwardly turned return bend 38 is formed in the trailing end of lateral heel 32 and said return bend terminates in a free leading end 40 that is angled upwardly, relative to horizontal plane 11. A convexity 41 is therefore formed near said free end 40 and said convexity is adapted to abut a support surface during ambulation. Convexity 41 performs the role of the bottom of a natural heel.

Medial heel 34 includes a heel extension 42 that is formed integrally and generally coplanar with sole 12. Return bend 44 is formed in the trailing end of heel extension 42 to provide a horizontal part 46. Medial vertically extending part 48 is formed integrally with horizontal part 46 and is perpendicular thereto. Like its lateral counterpart, lateral vertically extending part 26, medial vertically extending part 48 includes a lower part 50 having a breadth equal to the breadth of medial horizontal part 46 and a reduced breadth part 52.

Said reduced breadth part 52 provides a medial pylon support. Medial pylon connector 53 is secured to the trailing side of medial pylon support 52 and provides a means by which an elongate medial pylon is secured to novel foot 10.

As is best depicted in FIGS. 1 and 2, the trailing end of medial heel 34 trails the trailing end of lateral heel 32.

Slot 54 forms a space that separates lateral pylon support 30 from medial pylon support 52. Said slot 54 also separates lateral heel 32 and medial heel 34. Accordingly, lateral pylon support 30 responds to impact forces and other loads independently of medial pylon support 52, and vice versa.

More particularly, horizontal part 24 of ankle part 14 is supported from below by horizontal part 36 of lateral heel 32 as disclosed above. Lateral ankle part 14 has no corresponding medial ankle part as indicated in FIG. 3. Thus, the only support for medial pylon support is medial heel 34.

It is therefore clear that the unillustrated lateral pylon has substantially more support than the unillustrated medial pylon, with the desirable result that externally imparted forces are transferred from the lateral side of prosthetic foot 10 to the medial side thereof as is the case in a natural foot. This directs such forces toward the natural leg of the prosthetic foot user, as is desirable.

Moreover, the support of lateral ankle part 14 by horizontal part 36 of lateral heel 32 further ensures against a vertical bounce during ambulation.

This is the first prosthetic foot, anywhere in the world, having a two part heel that includes lateral heel 32, medial heel 34, and a lateral ankle part 14 supported from below by said lateral heel 32.

Figure 4:
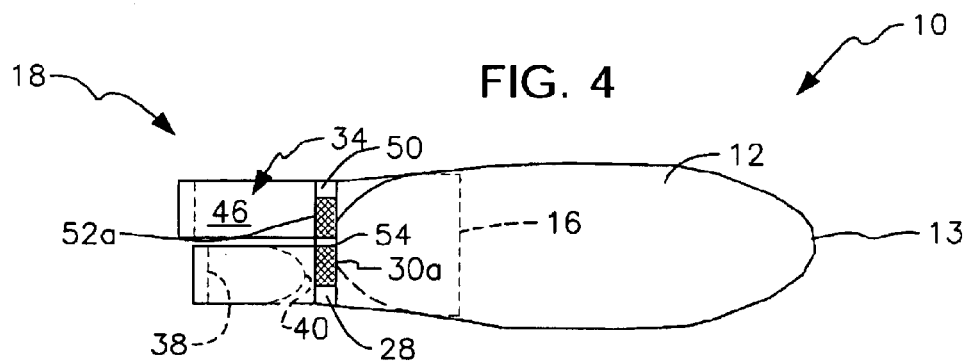
FIG. 4 is a top plan view of a second embodiment.
Figure 5:
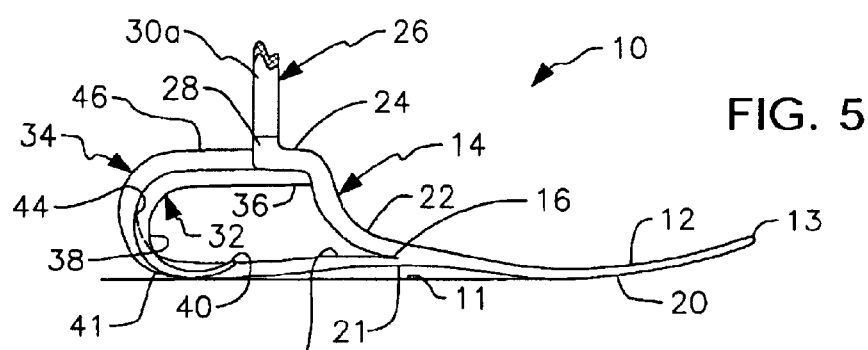
FIG. 5 is a side elevational view of the FIG. 4 embodiment.
Figure 6:
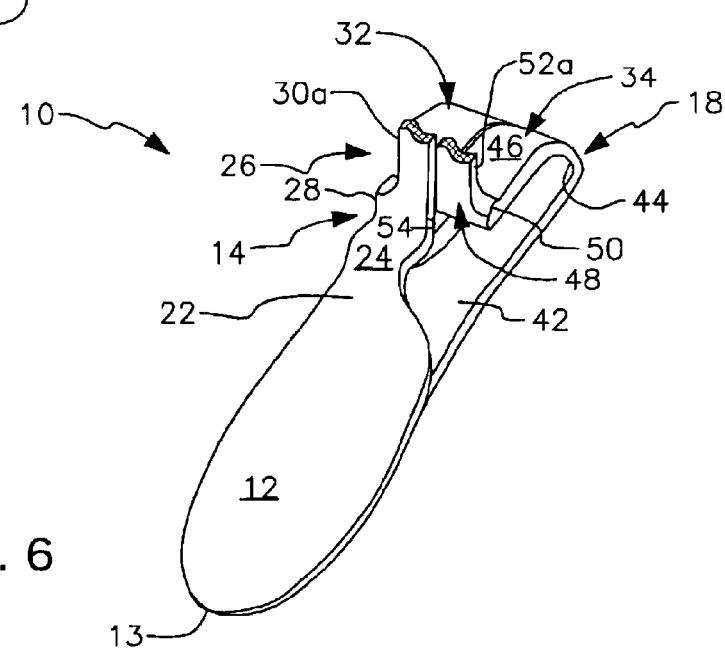
FIG. 6 is a perspective view of the FIG. 4 embodiment.

A second embodiment, depicted in FIGS. 4–6, has the same advantages as the first embodiment, but advantageously obviates pylon connectors 31 and 53. Pylon supports 30 and 52 are elongated to an extent of about twenty inches (20") and thus serve as lateral and medial pylons, 30a, 52a, respectively. A prosthetist cuts pylons 30a, 52a as needed when novel foot 10 is fitted to a residual limb.

Figure 7:
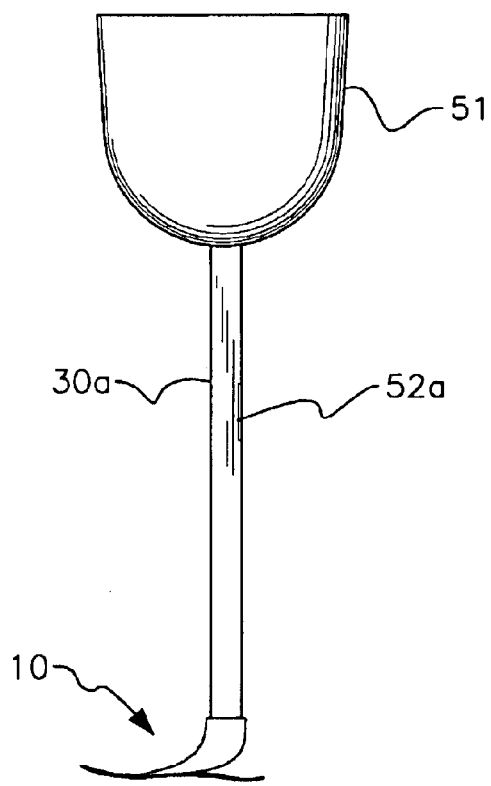
FIG. 7 is a perspective view of the elongate pylons embodiment when attached to a socket.

FIG. 7 depicts the novel structure when equipped with elongate pylons 30a, 52a.

After pylons 30a, 52a have been cut to a desired length, the prosthetist has several options by which the pylons may be connected to prosthetic socket 49. Pylons 30a, 52a may be laminated into prosthetic socket 51 as illustrated in said FIG. 7. This forms a permanent connection between pylons 30a, 52a and socket 51.

Figure 8:
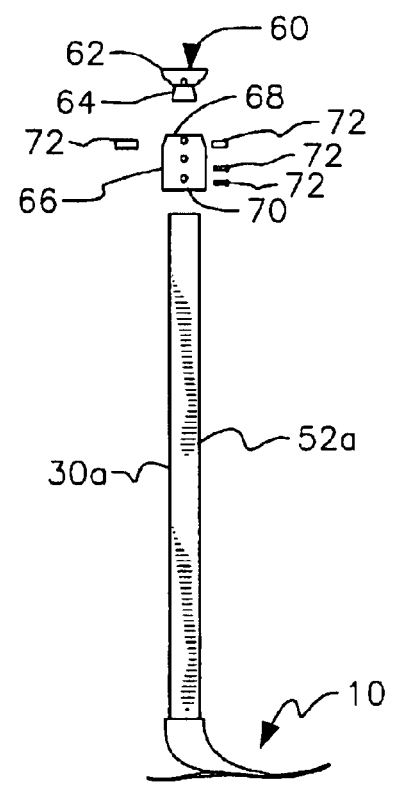
FIG. 8 is a perspective view of the elongate pylons embodiment and further depicting connector means, in exploded form, for connecting said elongate pylons to a socket.

A second option includes the use of a commercially available pyramid connector 60 as depicted in FIG. 8. Such pyramid connectors have been in use for fifty or so years. Pyramid connector 60 includes upper part 62 and lower part 64 that depends from the upper part. Upper part 62 is attached to the lowermost or distal end of socket 51. A hollow pyramid-receiving connector 66 has an open upper end 68 that receives lower part 64 of pyramid connector 60 and an open lower end 70 that receives the respective uppermost ends of pylons 30a, 52a. Lower end 64 of pyramid connector 60 and the respective upper ends of pylons 30a, 52a are captured in said hollow pyramid-receiving connector 66 by a plurality of set screws and other suitable fastening means, collectively denoted 72.

Pyramid connector 62 and pyramid-receiving connector 66 are employed to enable adjustment of the angle of pylons 30a, 52a so that prosthetic foot 10 falls in the correct medial/lateral and anterior/posterior planes, as perhaps best understood by making reference to FIGS. 7 and 8.

A third option available to the prosthetist after cutting pylons 30a, 52a to their correct length is to laminate the pylons to an unillustrated component and to attach that component to the socket.

Figure 9A:
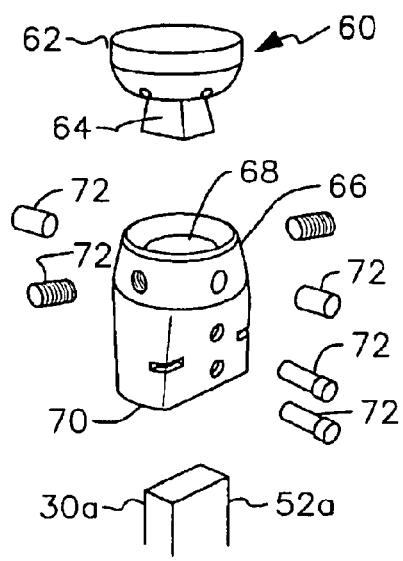
FIG. 9A is an exploded first perspective view of said connector means.
Figure 9B:
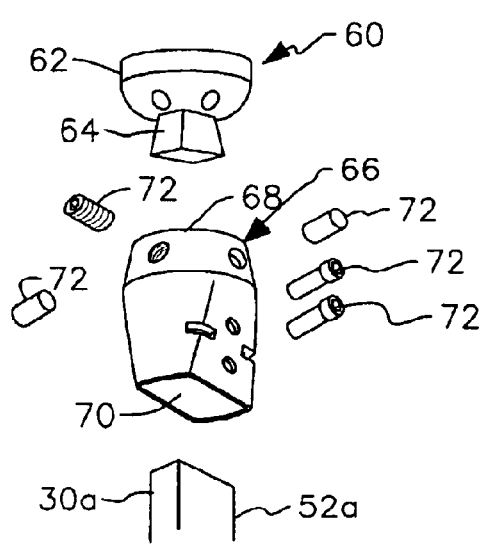
FIG. 9B is an exploded second perspective view of said connector means.
Figure 9C:
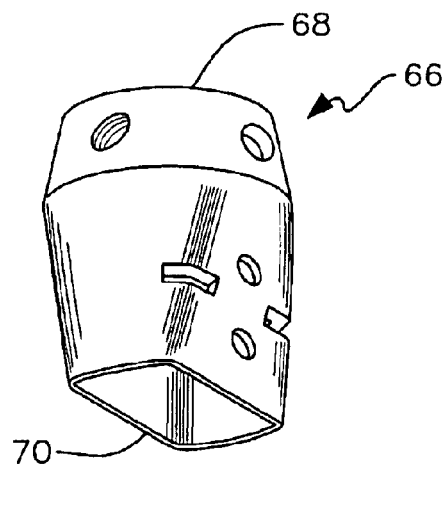
FIG. 9C is a first perspective view of a pyramid-receiving connector.
Figure 9D:
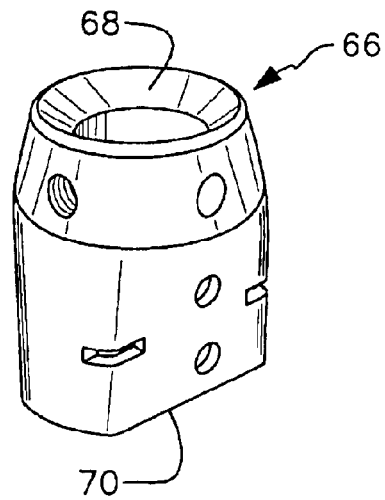
FIG. 9D is a second perspective view of said pyramid-receiving connector.

FIGS. 9A and 9B provide a more detailed perspective view of pyramid connector 60 and pyramid-receiving connector 66. FIGS. 9C and 9D provide a more detailed perspective view of pyramid-receiving connector 66.

Novel prosthetic foot 10 therefore exhibits a heel elasticity heretofore unknown. It enables a user to jog or run because its unique design absorbs high level impacts in the substantial absence of vertical, bouncing reaction. Moreover, it transfers forces from a lateral side to a medial side of the prosthetic foot, thereby decreasing the probabilities of a fall.

It will thus be seen that the objects set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A dynamic prosthetic foot having a split upper ankle and a heel with elasticity, comprising:

a sole, a lateral heel, and a medial heel;

a lateral ankle part that separates from said sole along a transverse parting line;

said lateral ankle part including a gradual upward bend, a horizontal part, and a vertically extending part;

said vertically extending part providing a lateral pylon support;

a lateral pylon connector secured to said lateral pylon support on a trailing side thereof;

said lateral heel having a leading part that underlies and supports said horizontal part of said ankle part;

a return bend formed in a trailing end of said lateral heel;

said return bend having a radius of curvature and said return bend terminating in a free leading end that is angled slightly upwardly relative to a horizontal plane so that a convexity near said free end is adapted to be in abutting engagement with a support surface during ambulation;

a medial heel extension formed integrally with said sole, said medial heel extension separating from said lateral ankle part along said transverse parting line;

said medial heel extension including a medial heel formed integrally with said medial heel extension;

said medial extension adapted to abut said support surface during ambulation;

said medial heel having a return bend formed therein, a horizontal part, and a vertically extending part formed integrally with said horizontal part;

said vertically extending part of said medial heel providing a medial pylon support;

a medial pylon connector secured to said medial pylon support on a trailing side thereof;

whereby said lateral heel and said medial heel provide differentiated elastic responses to impact forces created by ambulation.

2. The dynamic prosthetic foot of claim 1, wherein said horizontal part of said lateral ankle part and said horizontal part of said medial heel are co-planar with one another.

3. The dynamic prosthetic foot of claim 1, further comprising:
 a concavity formed about mid-length of said sole to perform the function of an arch of a natural foot.

4. The dynamic prosthetic foot of claim 1, further comprising:
 a convexity formed about mid-way between said concavity and a toe end of said prosthetic foot, said convexity performing the function of a ball of a natural foot.

5. The dynamic prosthetic foot of claim 1, wherein said transverse parting line is approximately half way between a leading end of said sole and a trailing end of said medial support.

6. The dynamic prosthetic foot of claim 1, wherein said medial support has a trailing end that trails the trailing end of said lateral support.

7. A dynamic prosthetic foot having a split upper ankle and a heel with elasticity, comprising:
 a sole, a lateral heel and a medial heel;
 a lateral ankle part that separates from said sole along a transverse parting line;
 said lateral ankle part including a gradual upward bend, a horizontal part, and a vertically extending part;
 said vertically extending part providing an elongate lateral pylon;
 a lateral heel having a leading part that underlies and supports said horizontal part of said ankle part;
 a return bend formed in a trailing end of said lateral heel;
 said return bend having a radius of curvature and said return bend terminating in a free leading end that is angled slightly upwardly relative to a horizontal plane so that a convexity near said free end is adapted to be in abutting engagement with a support surface during ambulation;
 a medial heel extension formed integrally with said sole, said medial heel extension separating from said lateral ankle part along said transverse parting line;
 said medial heel extension including a medial heel formed integrally with said medial heel extension;
 said medial extension adapted to abut said support surface during ambulation;
 said medial heel having a return bend formed therein, a horizontal part, and a vertically extending part formed integrally with said horizontal part;
 said vertically extending part of said medial support providing a medial pylon;
 whereby said lateral heel and said medial heel provide differentiated elastic responses to impact forces created by ambulation.

8. The dynamic prosthetic foot of claim 7, wherein said lateral pylon and said medial pylon are each about twenty inches in length.

9. The dynamic prosthetic foot of claim 7, wherein said horizontal part of said lateral ankle part and said horizontal part of said medial heel are co-planar with one another.

10. The dynamic prosthetic foot of claim 7, further comprising:
 a concavity formed about mid-length of said sole to perform the function of an arch of a natural foot.

11. The dynamic prosthetic foot of claim 7, further comprising:
 a convexity formed about mid-way between said concavity and a toe end of said prosthetic foot, said convexity performing the function of a ball of a natural foot.

12. The dynamic prosthetic foot of claim 7, wherein said transverse parting line is approximately half way between a leading end of said sole and a trailing end of said medial heel.

13. The dynamic prosthetic foot of claim 7, wherein said medial heel has a trailing end that trails the trailing end of said lateral heel.

14. The dynamic prosthetic foot of claim 7, wherein said lateral and medial pylons are laminated at respective uppermost ends thereof to a prosthetic socket.

15. The dynamic prosthetic foot of claim 7, wherein said lateral and medial pylons are connected at respective uppermost ends thereof to a connector member and wherein said connector member is laminated to a prosthetic socket.

16. The dynamic prosthetic foot of claim 7, wherein said lateral and medial pylons are connected at respective uppermost ends thereof to a pyramid-receiving connector that engages a pyramid that depends from said prosthetic socket.

* * * * *